United States Patent [19]

Choksi

[11] Patent Number: 4,737,144

[45] Date of Patent: Apr. 12, 1988

[54] SYRINGE WITH SELECTIVELY EXPOSED AND ENVELOPED NEEDLE

[76] Inventor: Pradip V. Choksi, 10935 Yolanda Ave., Northridge, Calif. 91326

[21] Appl. No.: 23,725

[22] Filed: Mar. 9, 1987

[51] Int. Cl.$^4$ .............................................. A61M 5/32
[52] U.S. Cl. ...................................... 604/198; 604/263
[58] Field of Search ................ 604/198, 197, 192, 263

[56] References Cited

U.S. PATENT DOCUMENTS

| | | | |
|---|---|---|---|
| 2,571,653 | 10/1951 | Bastien | 604/198 |
| 3,487,834 | 1/1970 | Smith, Jr. et al. | 604/197 X |
| 4,425,120 | 1/1984 | Sampson et al. | 604/198 |
| 4,655,751 | 4/1987 | Harbaugh | 604/198 |

Primary Examiner—John D. Yasko

[57] ABSTRACT

A syringe comprises:
(a) a tubular barrel,
(b) an injection needle mounted on the barrel to freely project forwardly thereof,
(c) a plunger slidable within the barrel and having a manually graspable retracting element at the rearward end of the barrel,
(d) and a sleeve mounted on the barrel to slide lengthwise from retracted position in which the needle is exposed, and an extended position in which the sleeve extends protectively about the needle,
(e) there being retention means associated with the sleeve and barrel to retain the sleeve in said forwardly extended position when advanced thereto from said retracted position.

6 Claims, 3 Drawing Sheets

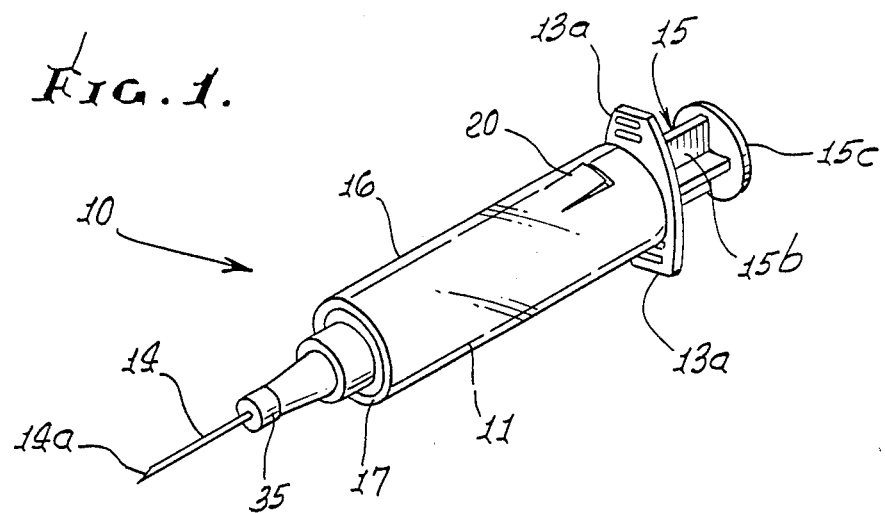
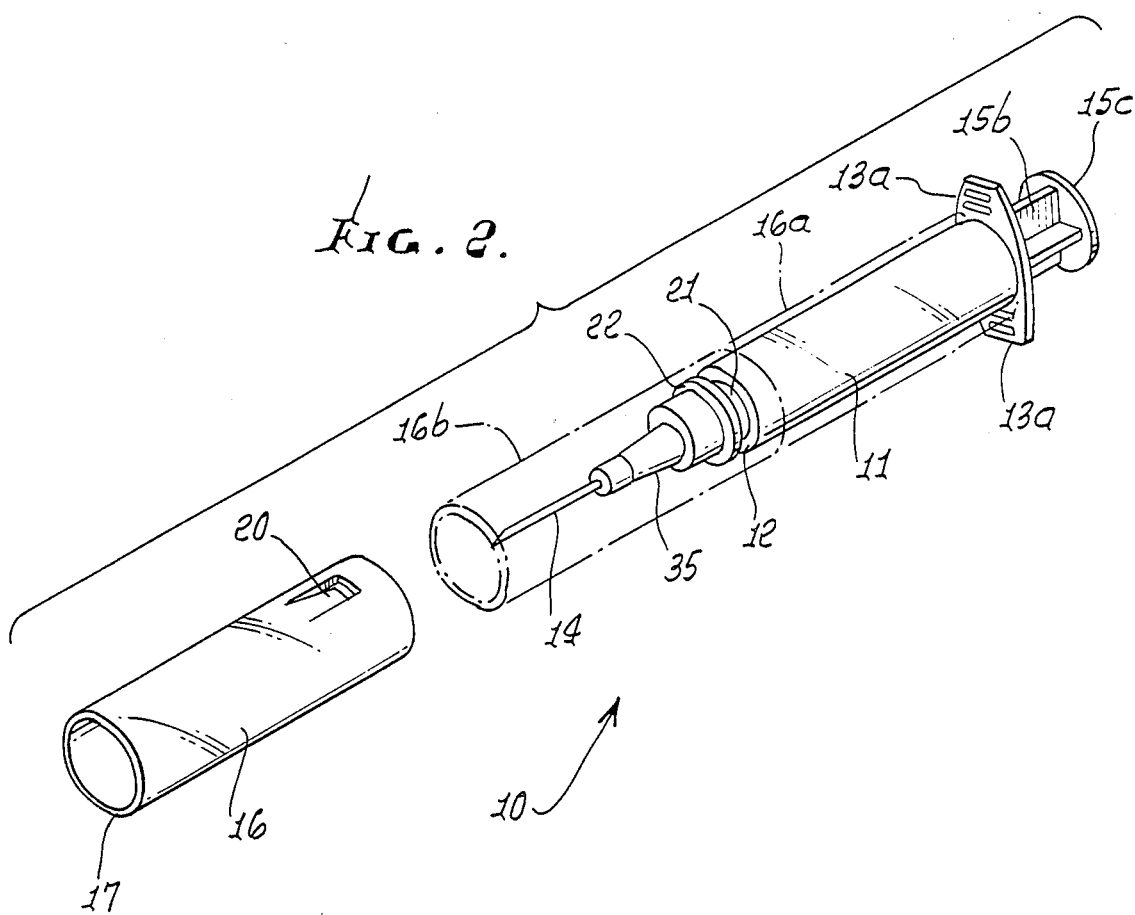

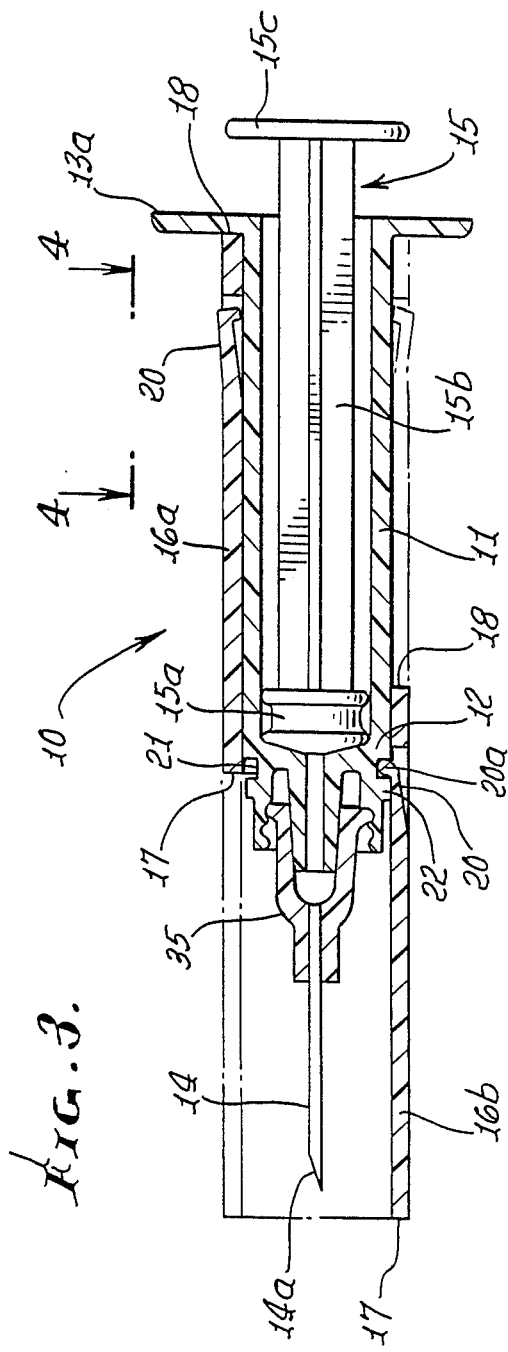
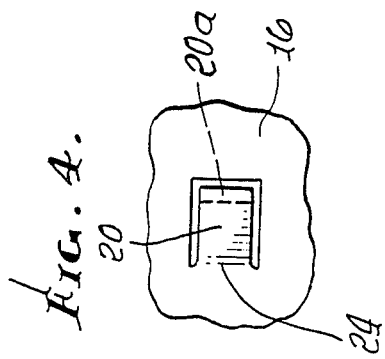
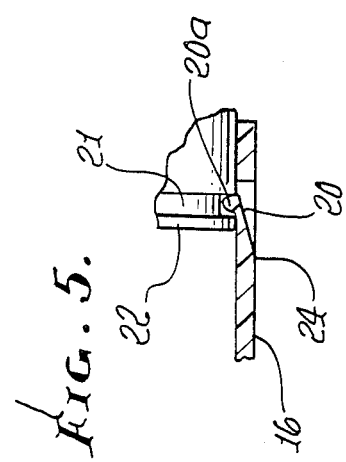

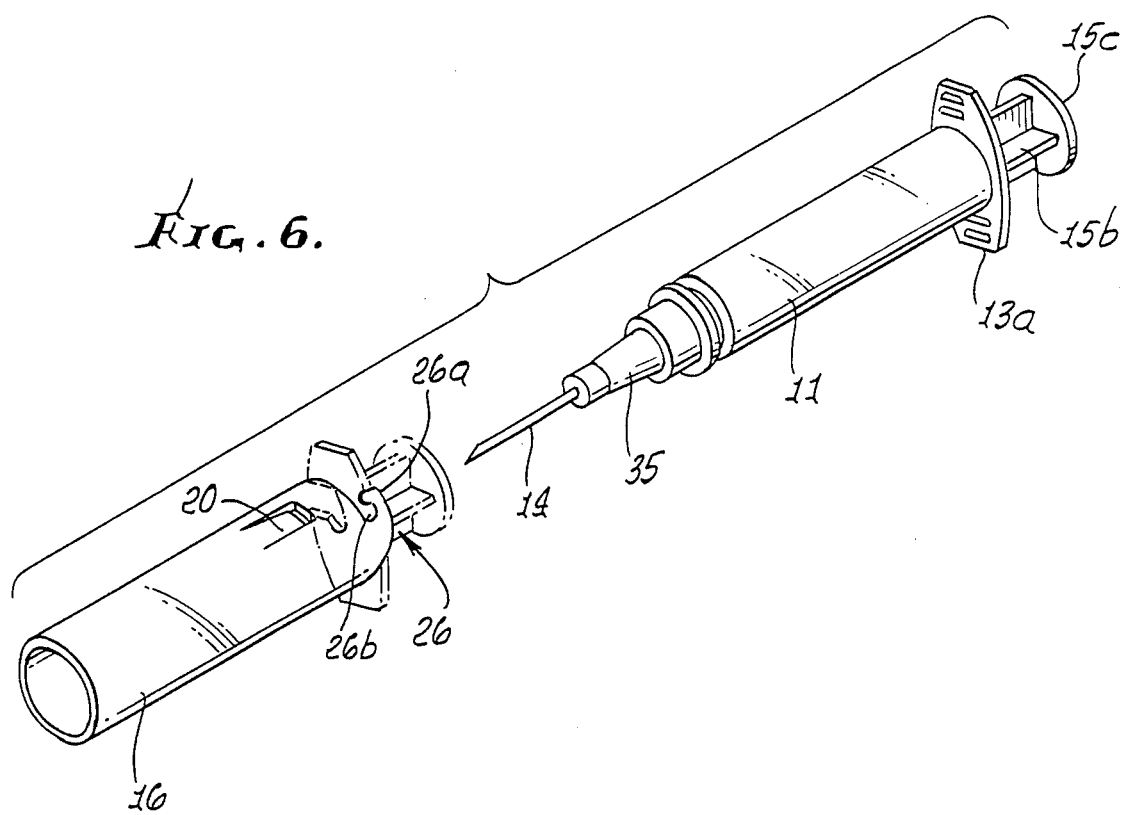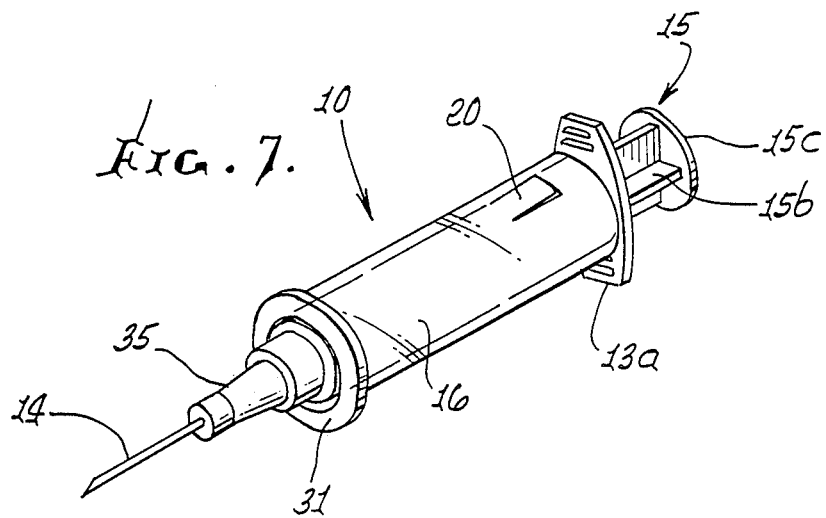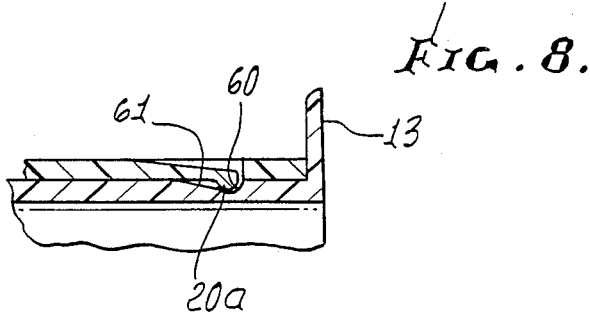

SYRINGE WITH SELECTIVELY EXPOSED AND ENVELOPED NEEDLE

BACKGROUND OF THE INVENTION

This invention relates generally to syringe structures, and more particularly to protective means on syringes to prevent accidental manual engagement with the syringe needle.

PROBLEM DEFINITION

A large number of hypodermic needles are used in hospitals for administering medications to patients. These must be discarded safely after use. It is imperative to prevent accidental puncturing of hospital personnel with a used needle.

The needles are supplied by the manufacturer in a protective cap that resembles a tube. This cap is usually made of molded plastic and fits snugly on the hub of the needle.

To use the needle, it is attached to a syringe with the protective cap still in place. If the hospital pharmacy prepares the medications for dispensing, then the pharmacist removes the needle cap and aspirates medication from the vial into the syringe. The needle is carefully re-capped, labelled, and sent to the nurse. Accidental puncturing of the pharmacist during needle re-capping at this time is not considered a great risk because the needle is sterile. If accidental puncture occurs at this time, then the needle/syringe assembly is discarded. In some hospitals, these steps are carried out by the nurse instead of the pharmacist. Once the medication is in the syringe, the nurse is ready to administer it to the patient. The nurse removes the needle cap and sets it aside. The patient's skin is punctured and medication is injected. The needle is then withdrawn from the patient. The used needle, which is still attached to the syringe, is recapped and taken back to the nursing station for disposal.

Hospital statistics show that during re-capping of the syringe needle, the chance of accidental puncture is quite substantial. This is because the opening of the cap is very small (about ¼ inch diameter). A second cause of accidental puncture is the technique of re-capping. The cap is grasped in one hand and the syringe in the other, and if the tip of the needle misses the opening of the cap then it is very likely to puncture the fingers that are grasping the cap. This problem is critical when the syringe and needle contain dangerously contaminating fluids.

SUMMARY OF THE INVENTION

It is a major object of the invention to provide a simple, effective solution to the above problem. Basically, the invention contemplates the provision of:

(a) a tubular barrel, (b) an injection needle mounted on the barrel to freely project forwardly thereof, (c) a plunger slidable within the barrel and having a manually graspable retracting element at the rearward end of the barrel, (d) and a sleeve mounted on the barrel to slide lengthwise from retracted position in which the needle is exposed, and an extended position in which the sleeve extends protectively about the needle, (e) there being retention means associated with the sleeve and barrel to retain the sleeve in said forwardly extended position when advanced thereto from said retracted position.

Typically, the protective sleeve or sheath fits snugly around the barrel of the syringe, and can be pushed axially forward to envelope the needle after medication is administered. Several embodiments of this sliding sheath concept are possible, each one effectively protecting the needle and preventing acccidental puncture. The sheath is preferably made of a clear plastic material to permit visualization of the contents of the syringe and volume graduation markings.

The procedure for administering the medication and disposing the syringe/needle assembly is as follows:

a. Remove protective cap from the needle and aspirate medication into the syringe.

b. Make puncture into the patient's skin and inject medication.

c. Remove needle from the patient.

d. Slide the sheath forward until it locks in the forward position. In this position, it completely envelopes the needle. The sheath cannot be retracted once it is in this position.

e. Discard the assembly.

Multiple advantages are afforded, and are as follows:

1. The sheath never leaves the syringe barrel. It is available for protecting the needle immediately after the syringe is used.

2. The motion of engaging the sheath in the forward locked position is simple and is unlikely to result in accidental punctures common with conventional needle caps.

3. The sheath cannot retract to expose the needle once it is locked in place. This prevents accidental punctures to all personnel in the product disposal procedure.

4. The sheath is unobtrusive and does not require the operator to change the injection technique.

5. The needles for the procedure are of standard configuration.

6. The sheath can be incorporated into the syringe manufacturing process quite easily for very little additional cost.

7. The sheath can be fitted into syringes of all sizes and manufacture.

These and other objects and advantages of the invention, as well as the details of an illustrative embodiment, will be more fully understood from the following specification and drawings, in which:

DRAWING DESCRIPTION

FIG. 1 is a perspective view of a syringe incorporating the invention;

FIG. 2 is a view like FIG. 1, but with certain elements shown in exploded form;

FIG. 3 is a side elevation, in section, showing a protective sleeve in retracted and adanced positions, relative to the syringe barrel;

FIG. 4 is a fragmentary bottom plan view showing a lock tab on the sleeve and taken on lines 4—4 of FIG. 3;

FIG. 5 is a fragmentary view showing details of lock tab retention of the sleeve in advanced position;

FIG. 6 is like FIG. 2, showing a modified lock; and

FIG. 7 is a view like FIG. 1, showing a protection flange on the protective sleeve; and FIG. 8 is a modification.

DETAILED DESCRIPTION

In FIGS. 1-3 a syringe 10 includes a tubular barrel 11 having walls 12 and 13 at its opposite ends. Lateral wings 13a at rear wall 13 allow finger gripping of the syringe, during use. A hollow needle 14 is mounted on the barrel, as by structure 35 at the front of wall 12, so that the needle freely projects forwardly of the barrel. A needle tip appears at 14a, and is typically sharp. A plunger 15 is slidable within the barrel, and includes a piston end 15a, a piston rod 15b, and a manually graspable, retraction element 15c at the rear of the barrel. For example, as the element 15c is drawn rearwardly, liquid is drawn into the barrel via the needle the tip of which is immersed in a supply of the liquid.

In accordance with the invention, a tubular sleeve 16 is mounted on the barrel to slide axially lengthwise, while guided by the barrel outer surface, from a retracted position as indicated at 16a in FIG. 4 to an extended position as indicated at 16b. In retracted position the forward end 17 the sleeve is typically near barrel end wall 12, and the rearward end 18 of the sleeve is typically near the barrel rear wall; whereas in extended position, the forward end 17 is beyond the needle tip, and the rearward end 18 of the sleeve overlaps the forwardmost extent of the barrel. Accordingly, in such extended position of the sleeve, the needle is protectively enclosed by the tubular envelope of the sleeve, but can be seen as the sleeve typically consists of transparent plastic.

Means associated with the barrel and sleeve to retain it in forwardmost position may comprise static friction generated by engagement of the sleeve base and the barrel outer surface, at the overlap as referred to. The syringe user is thus protected against inadvertent manual contact with the enveloped needle, including its sharp tip 14a spaced inwardly of the sleeve end 17, as shown. FIG. 1 may be considered as representative of a syringe wherein such friction retention of the sleeve is employed.

FIGS. 2-5 may be considered as representative of a syringe wherein such means to retain the sleeve in extended position includes or comprises at least one detent carried by one of the sleeve and barrel, and a slot on the other of the sleeve and barrel, to receive the detent when the sleeve is advanced to extended position. As actually shown, the detent means comprises two tabs 20 which are effectively spring urged and carried by the sleeve, together with slot means on the barrel near its forward end for reception of end portion 20a of the tabs when the sleeve is advanced to extended position indicated at 16b. The tabs may be integral with the sleeve wall, as shown. That slot means advantageously takes the form of an annular recess 21 sunk or formed radially inwardly at the forward end of the barrel between end wall 12 and an exterior flange 22 spaced forwardly of wall 12; thus, endwise antirotational guided movement of the sleeve is not necessary, as the tab end portion 20a will be urged into the recess no matter what relative rotation of the sleeve and barrel occurs. The tabs are cantilevered in their support at 24 by the sleeve, and spring urged at 24 to normally flex inwardly, as indicated in FIG. 5. The tabs are located at diametrically opposite sides of the sleeve. Once the tab end portions deflect into the recess upon sleeve extension leftwardly to position 16b, the sleeve is locked in position, protectively enveloping the needle, as shown. Wall 12 blocks rightward movement of the tabs and sleeve, as is clear from FIG. 5, and flange 22 blocks leftward movement of the tab end portion 20a.

In FIG. 6 the construction is the same, excepting that the retention means also includes bayonet lock elements indicated generally at 26, providing additional connection of the sleeve and barrel. That connection includes bayonet tongue 26a on the sleeve rotatable behind a tongue 26b on the barrel, when the sleeve is in extended position 16b as seen in FIG. 3.

FIG. 7 illustrates provision of an exterior flange 31 on the sleeve proximate its forward end 18. That flange prevents accidental manual slippage beyond the sleeve forward end and into contact with the needle, as the sleeve is extended, or when the sleeve is manually grasped initially, as in its retracted position, as shown.

FIG. 8 shows a modification in which an annular recess is formed at 60 in and about the barrel, near the end wall 13. The recess is sized to radially inwardly receive and store the end portions 20a of the tabs 20, in rearwardly retracted position of the sleeve 16, thereby preventing inadvertent forward travel of the sleeve on the barrel while the needle is in use. Also, this allows the tabs to be unflexed, i.e. strain free, during such tab storage, which is of advantage as during sterilization since heating tends to promote or effect undesired stress relief. A frusto-conical ramp 61 on the barrel guides the tab end portions radially outwardly toward the barrel cylinder surface, as the sleeve is displaced endwise forwardly toward 16b position.

I claim:

1. In a syringe, the combination comprising:
   (a) a tubular barrel,
   (b) an injection needle mounted on the barrel to freely project forwardly thereof,
   (c) a plunger slidable within the barrel and having a manually graspable retracting element at the rarward end of the barrel,
   (d) and a sleeve mounted on the barrel to slide lengthwise from retracted position in which the needle is exposed, and an extended position in which the sleeve extends protectively about the needle,
   (e) there being retenting means associated with the sleeve and barrel to retain the sleeve in said forwardly extended position when advance thereto from said retracted position, said retention means comprising two spring urged tabs carried by the sleeve to define cantilever arms, and slot means on the barrel near the forward end thereof for reception of portions of the tabs when the sleeve is advanced to said extended position,
   (f) said slot means comprising a first annular recess extending about an axis defined by the barrel, there being an annular shoulder on the sleeve and proximate said recess for blocking movement of the tabs and sleeve in a sleeve retracting direction when said portions of the tabs are received in the recess,
   (g) and including an additional and annular slot formed in the barrel near the rearward end thereof for radially inward storing reception of said portions of the tabs when the sleeve is in said retracted position,
   (h) and a ramp on the barrel intersecting said additional slot and the outer surface of the barrel, for guiding said tab portions.

2. The combination of claim 1 wherein the sleeve extends from said barrel to a point beyond the tip of the needle, in said extended position.

3. The combination of claim 1 wherein there is a flange shoulder on the barrel at the forward side of the first annular recess to block forward movement of the tab portions and the sleeve when said portions of the tabs are received in the first recess.

4. The combination of claim 1 wherein said retention means comprises interfittable bayonet like elements on the sleeve and barrel.

5. The combination of claim 1 including an exterior flange on the sleeve proximate the forward end thereof to prevent accidental manual slippage beyond the sleeve forward end and into contact with the needle when the sleeve is manually grasped.

6. The combination of claim 1 wherein the barrel and sleeve both consist of transparent plastic material.

* * * * *